(12) United States Patent
Takikawa et al.

(10) Patent No.: US 8,794,070 B2
(45) Date of Patent: Aug. 5, 2014

(54) METHOD FOR ANALYZING VIBRATION PROPERTY OF MEMBER INCLUDING PIEZOELECTRIC ELEMENT

(75) Inventors: Kenichi Takikawa, Aikoh-gun (JP); Toshiki Ando, Aikoh-gun (JP)

(73) Assignee: NHK Spring Co., Ltd., Kanagawa (JP)

( * ) Notice: Subject to any disclaimer, the term of this patent is extended or adjusted under 35 U.S.C. 154(b) by 269 days.

(21) Appl. No.: 13/451,033

(22) Filed: Apr. 19, 2012

(65) Prior Publication Data

US 2013/0098156 A1 Apr. 25, 2013

(30) Foreign Application Priority Data

Jun. 23, 2011 (JP) ................................. 2011-139930

(51) Int. Cl.
*G01N 29/12* (2006.01)

(52) U.S. Cl.
USPC .............................................. 73/579; 73/649

(58) Field of Classification Search
USPC .................................................... 73/579, 649
See application file for complete search history.

(56) References Cited

U.S. PATENT DOCUMENTS

| | | | | |
|---|---|---|---|---|
| 5,032,754 A | * | 7/1991 | Iwao et al. | 310/323.02 |
| 5,237,237 A | * | 8/1993 | Ueda et al. | 310/323.08 |
| 6,087,760 A | * | 7/2000 | Yamaguchi et al. | 310/334 |
| 8,018,670 B1 | * | 9/2011 | Ito et al. | 360/31 |
| 8,306,793 B2 | * | 11/2012 | Huang et al. | 703/2 |

FOREIGN PATENT DOCUMENTS

| | | | |
|---|---|---|---|
| JP | 363075624 | * | 4/1988 |
| JP | 09015086 | * | 1/1997 |
| JP | 2002-050140 | | 2/2002 |
| JP | 2005006763 | * | 1/2005 |
| JP | 200870302 | * | 3/2008 |

* cited by examiner

*Primary Examiner* — J M Saint Surin
(74) *Attorney, Agent, or Firm* — Jordan and Hamburg LLP (57) ABSTRACT

A method for accurately and speedy analyzing vibration property of head suspension including a piezoelectric element that moves a head according to voltage application. The method comprises a displacement obtaining step obtaining displacement of each node point of the piezoelectric element by voltage application to the piezoelectric element, a reaction force obtaining step eliminating the voltage application and applying the obtained displacement to each node point, a reaction force applying step eliminating the applied displacement and applying obtained reaction force to each node point, and an analyzing step performing the frequency response analysis by using mode superposition method.

4 Claims, 9 Drawing Sheets

METHOD FOR ANALYZING VIBRATION PROPERTY OF MEMBER INCLUDING PIEZOELECTRIC ELEMENT

BACKGROUND OF THE INVENTION

1. Field of the Invention

This invention relates to a method for analyzing vibration property of a member, such as a head suspension, including a piezoelectric element.

2. Description of the Related Art

In a hard disk drive (also referred to as "HDD"), a head suspension is attached to a carriage and supports a head including a read/write element. In recent years, high-performance HDDs are required, and due to this, it is important to control vibration property of a head suspension.

To control the vibration property, transfer function of the head suspension is calculated with frequency response analysis. The frequency response analysis employs mode superposition method in order to reduce calculation time.

The mode superposition method assumes that the vibration caused by external force can be described by superposing two solutions; forced vibration solution largely depending on the frequency of external force, and natural vibration solution based on specific vibration to each object. By using the mode superposition method, the calculation time for the frequency response analysis can be significantly reduced.

In recent years, there are also HDDs employing a dual actuator system with a dual actuator-type head suspension. Such dual actuator system has a piezoelectric element in addition to a voice coil motor that drives a carriage. The piezoelectric element is made of, for example, lead zirconate titanate (PZT) and is fixed at the part between a base plate and a load beam, or at a tongue of the head suspension. Therefore, the head can be moved slightly in a sway direction relative to the base plate with the piezoelectric element deformed in response to voltage applied thereto.

For the dual actuator-type head suspension, the frequency response analysis based on the applied voltage to the piezoelectric element is also required.

Figure 10:
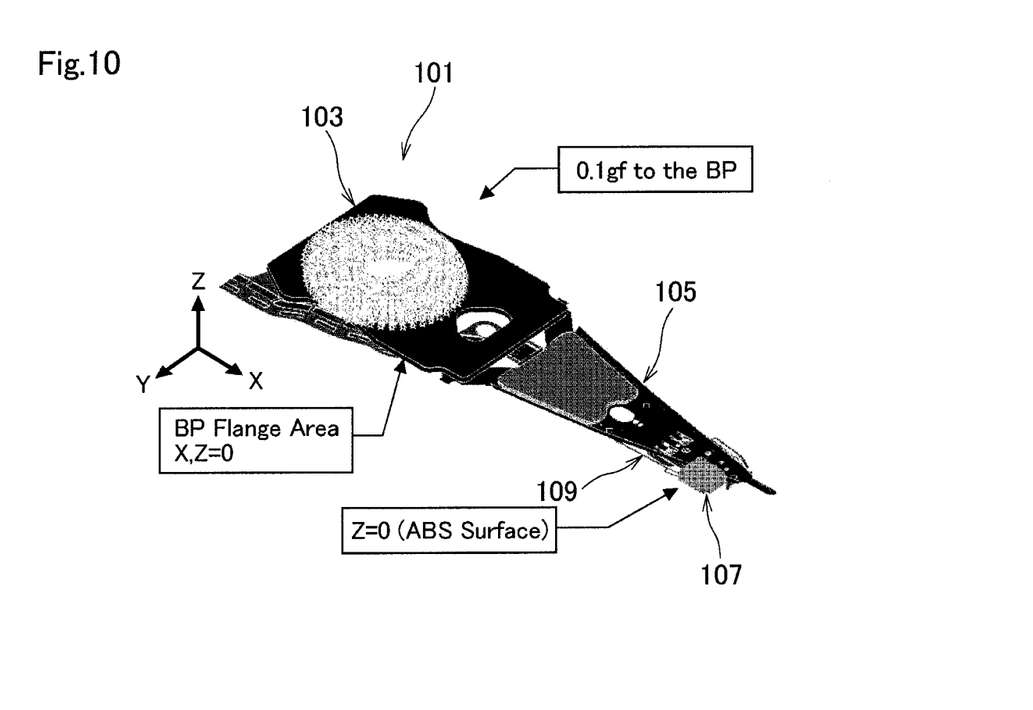
FIG. 10 is a perspective view illustrating a head suspension with a base plate excited for frequency response analysis according to related art.
Figure 11:
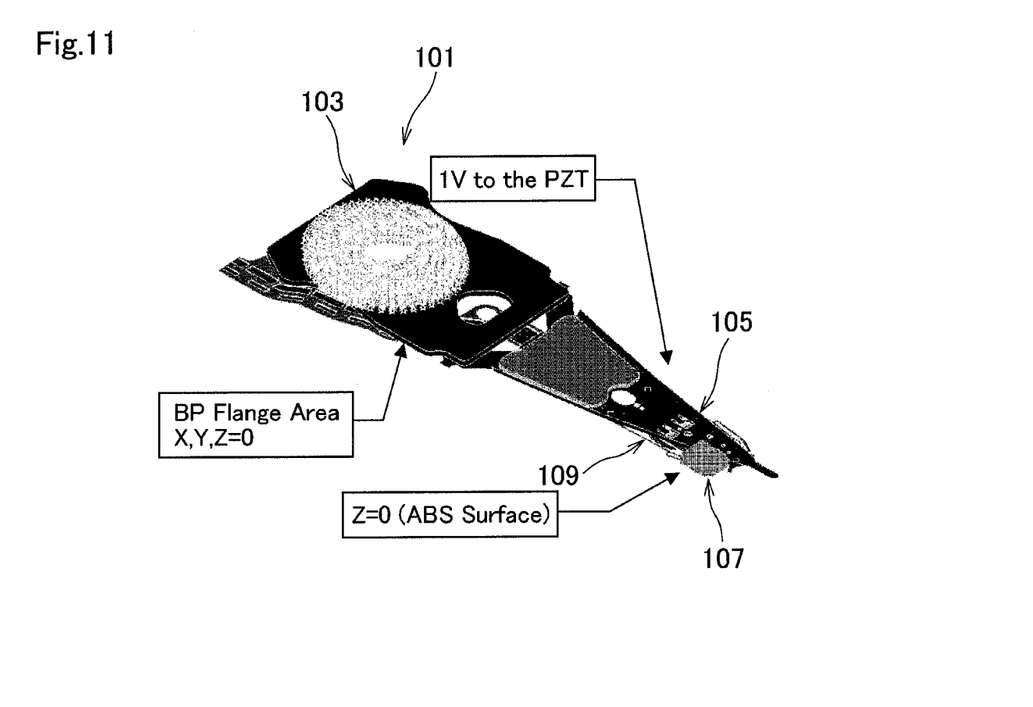
FIG. 11 is a perspective view illustrating the head suspension with a piezoelectric element to which voltage is applied for frequency response analysis according to related art.

FIGS. 10 and 11 are perspective views respectively illustrating external force application and voltage application to a head suspension 101 having a piezoelectric element. The head suspension 101 comprises a base plate 103, a load beam 105 and a flexure 109 supporting a head 107 on a tongue. The piezoelectric element is fixed at the tongue of the flexure 109.

The head suspension 101 is fixed to the carriage through the base plate 103 and is turned by the voice coil motor. Based on this structure, Y-directional 0.1 gf exciting force is applied to the head suspension 101 for the frequency response analysis as illustrated in FIG. 10. In this case, X and Z-directional exciting forces applied for the base plate 103 are kept as "0", and also Z-directional exciting force applied for the head 107 is kept as "0".

In the case that Y-directional 0.1 gf exiting force is applied for the head suspension, the vibration property is obtained by the frequency response analysis within the short time such as within 10 minutes, by using above-mentioned mode superposition method.

On the other hand, the head suspension 101 slightly moves the head 107 with the piezoelectric element to which voltage is applied. Based on this structure, voltage of 0.1V is applied to the piezoelectric element for the frequency response analysis. In this case, X, Y and Z-directional exciting forces applied for the base plate 103 are kept as "0", and also Z-directional exciting force applied for the head 107 is kept as "0".

The frequency response analysis of the piezoelectric analysis of the piezoelectric element, however, generally requires direct time integration method, also called full method, in which equation of motion is directly solved. This is because of that the piezoelectric analysis of the piezoelectric element is a coupled analysis between electric field and structure and the mode superposition method cannot be used for the frequency response analysis of the piezoelectric analysis.

The full method requires equation of motion to be solved for each frequency and significantly long time for calculation.

For example, in case that the equation of motion is solved for each 100 Hz up to 50 kHz, it requires 500 times calculation, 50,000 divided by 100. Each calculation requires 3 minutes, so that 500 times calculation requires 500 times 3 minutes, in other word 1,500 minutes or 25 hours, in total.

On the other hand, when using mode superposition method, modal analysis is previously performed to calculate mode vector and so on.

In the piezoelectric analysis of piezoelectric element, the mode superposition method involves two modes to be calculated. One of the two modes is short-circuit condition also referred to as resonant condition in which no voltage is applied for both electrode of the piezoelectric element. Another mode is open-circuit condition also referred to as antiresonant condition in which voltage is applied for one of two electrodes.

For calculating above-mentioned two modes, it requires different constraint conditions, therefore the mode superposition method cannot be applied for calculating the two modes.

The mode superposition method may be applied for calculating transfer function by using the result of one of the two modes, resonant condition mode and antiresonant condition mode. This reduces the accuracy of the calculation.

SUMMARY OF THE INVENTION

An object of the present invention is to provide a method for accurately and speedy analyzing vibration property of a member including a moving portion and a piezoelectric element that moves the moving portion according to voltage application while using frequency response analysis.

To accomplish the object, an aspect of the present invention provides the method for analyzing vibration property of a member including a moving portion and a piezoelectric element that moves the moving portion according to voltage application comprises a displacement obtaining step obtaining displacement of each node point of the piezoelectric element by voltage application to the piezoelectric element, a reaction force obtaining step eliminating the voltage application and obtaining reaction force of each node point of the piezoelectric element by applying the obtained displacement to the piezoelectric element, a reaction force applying step eliminating the applied displacement and applying obtained reaction force to each point of the piezoelectric element, and an analyzing step performing the frequency response analysis by using mode superposition method.

This aspect of the present invention obtains vibration property according to the result of the frequency response analysis by using the mode superposition method based on the reaction force. The obtained vibration property approximates to natural vibration property exhibited by applying voltage to the piezoelectric element. This enables vibration property the member to be accurately managed.

In addition, this aspect performs frequency response analysis by using mode superposition method, so that vibration property of the member is obtained in a short time.

DETAILED DESCRIPTION OF EMBODIMENTS

Hereinafter, embodiments of method for analyzing vibration property of a member according to the present invention will be described with reference to the drawings.

Each embodiment accurately carries out frequency response analysis of a member in a short time while using frequency response analysis, the member including a moving portion and a piezoelectric element that moves the moving portion according to voltage application. Each embodiment comprises steps of obtaining displacement of each node point of the piezoelectric element by voltage application to the piezoelectric element, a eliminating voltage application and obtaining reaction force by applying the obtained displacement to each node point, eliminating the displacement and applying the obtained reaction force to the each node point of the piezoelectric element, and performing frequency response analysis by using mode superposition method according to the applied reaction force.

The first embodiment will be explained in detail with reference to FIGS. 1 to 6B.

Figure 1:
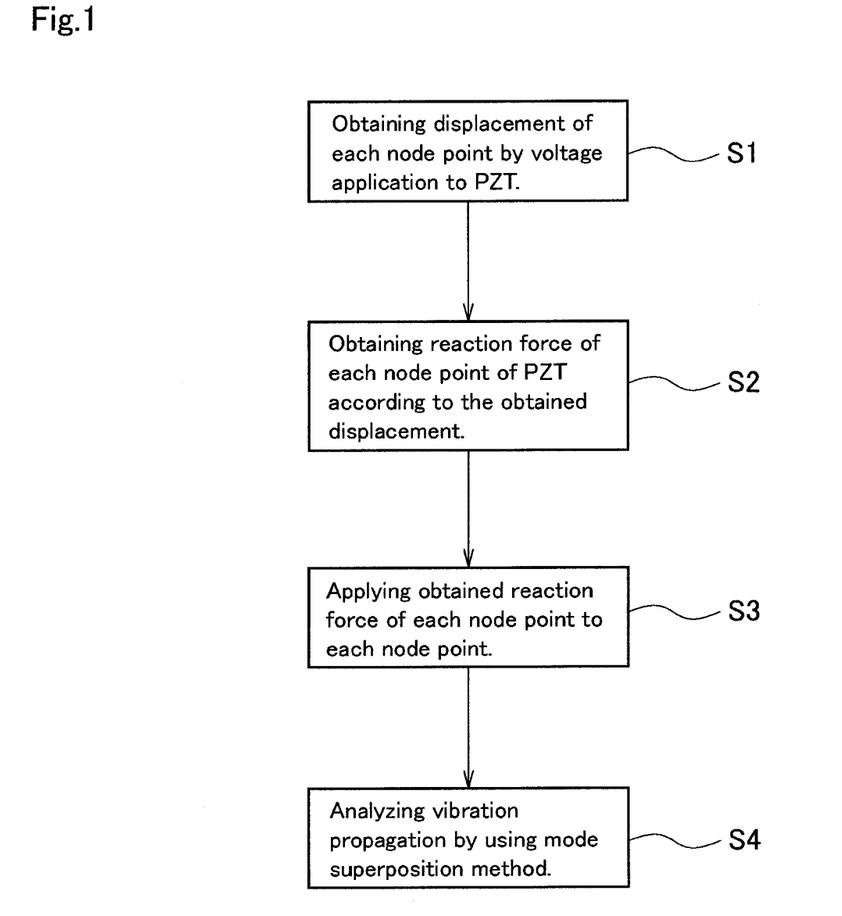
FIG. 1 is a flowchart illustrating vibration property analysis of a member according to a first embodiment.

FIG. 1 is a flowchart illustrating vibration property analysis of a member.

As illustrated in FIG. 1, a method for analyzing vibration property of a member according to this embodiment is used for analyzing a head suspension to be incorporated in HDD. The head suspension as the member in this embodiment includes a head and a piezoelectric element made of, for example, lead zirconate titanate also called PZT and so on, so that the piezoelectric element deforms in response to voltage applied thereto to slightly move the head as a moving portion.

The method for analyzing vibration property according to this embodiment comprises a displacement obtaining step S1 as first obtaining step, a reaction force obtaining step S2 as second obtaining step, a reaction force applying step S3 as an applying step, and an analyzing step S4.

In the displacement obtaining step S1, the method applies voltage to the piezoelectric element, to deform the piezoelectric element while displacing each node point thereof. In this state, i.e., by voltage application to the piezoelectric element, the method obtains displacement of each node point of the piezoelectric element. The displacement is obtained by performing static analysis.

In the reaction force obtaining step S2, the voltage application in S1 is eliminated and the obtained displacement of each node point is applied to corresponding one of the node points to generate reaction force at each node point. The reaction force of each node point of the piezoelectric element is obtained in this state, i.e., by applying the obtained displacement in step S1 to each node point. The reaction force is obtained by performing static analysis.

In the reaction force applying step S3, the applied displacement in S2 is eliminated and the obtained reaction force of each node point is applied to corresponding one of the node points of the piezoelectric element.

In the analyzing step S4, frequency response analysis is performed by using mode superposition method according to the applied reaction force in S3.

Each of the four steps S1 to S4 may be performed sequentially or successively by using macro program and the like.

Figure 2:
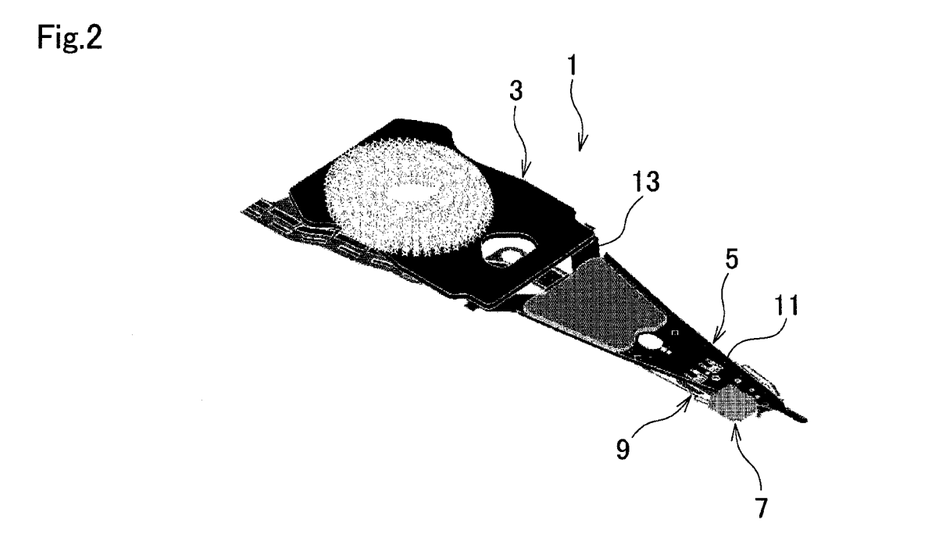
FIG. 2 is a perspective view illustrating a head suspension that is the member according to the first embodiment.
Figure 3:
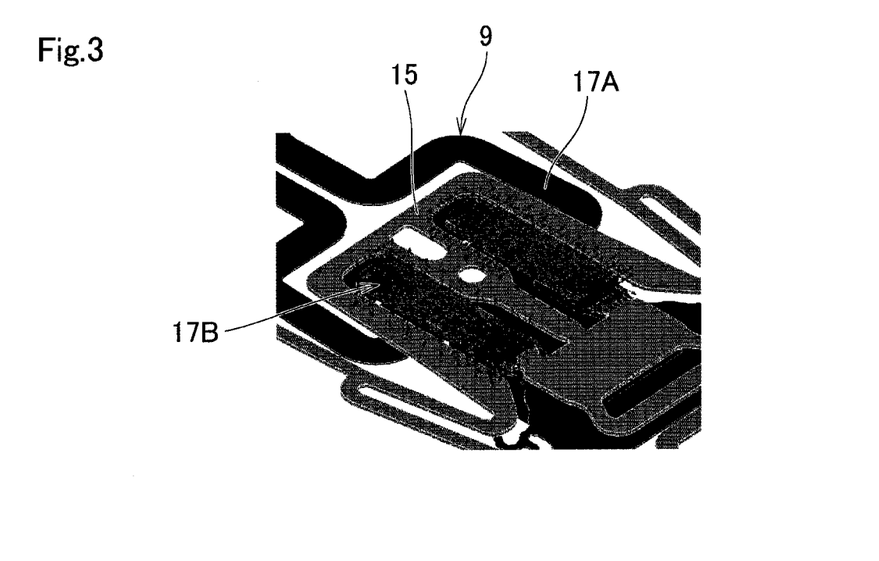
FIG. 3 is an enlarged perspective view illustrating a piezoelectric element on a tongue and the surrounding area of the head suspension according to the first embodiment.
Figure 4:
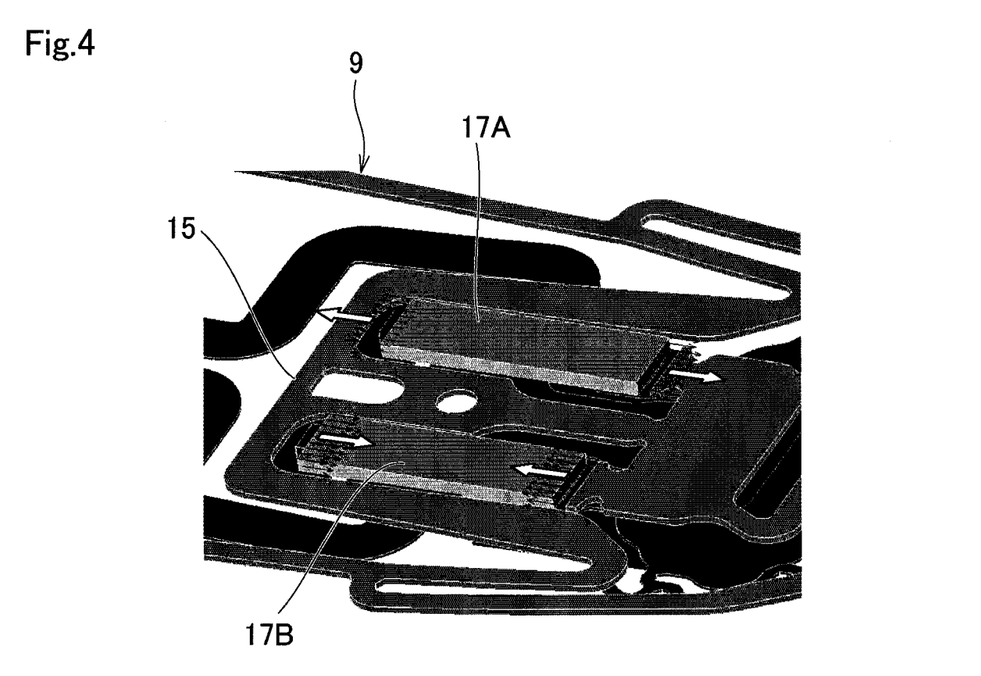
FIG. 4 is an enlarged perspective view illustrating the piezoelectric element on the tongue and the surrounding area of the head suspension according to the comparative example.
Figure 5A:
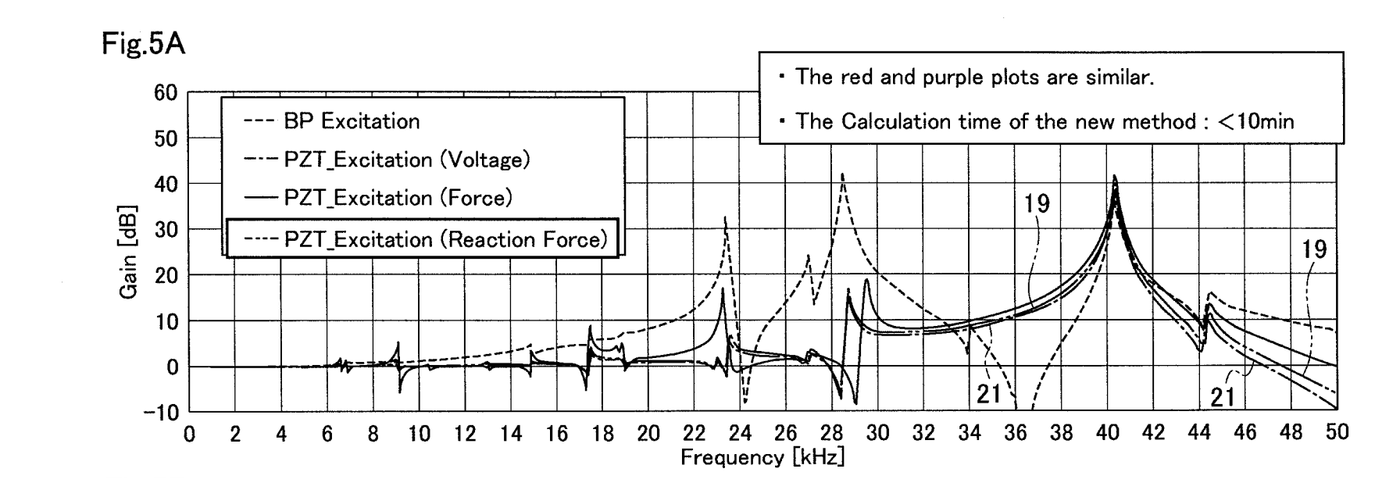
FIG. 5A is a gain diagram obtained by frequency response analysis according to the first embodiment.
Figure 5B:
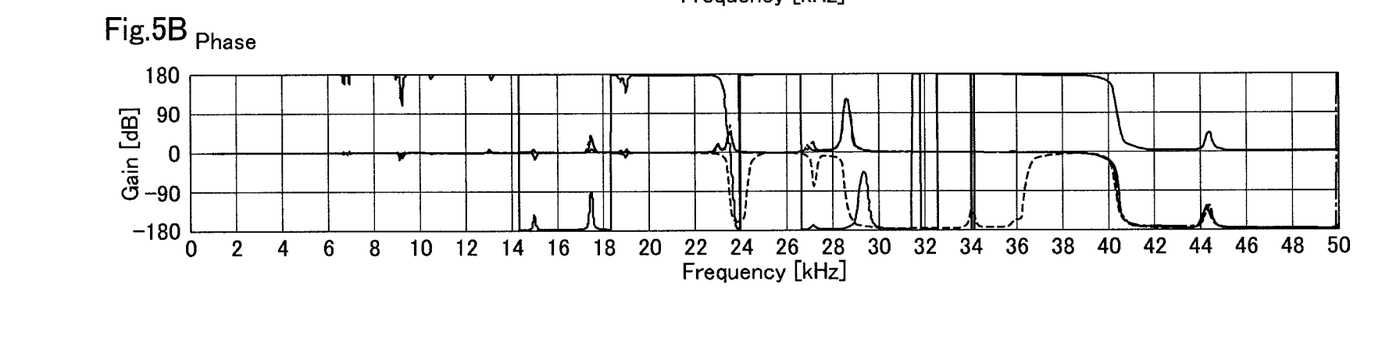
FIG. 5B is a phase diagram obtained by frequency response analysis according to the first embodiment.
Figure 6A:
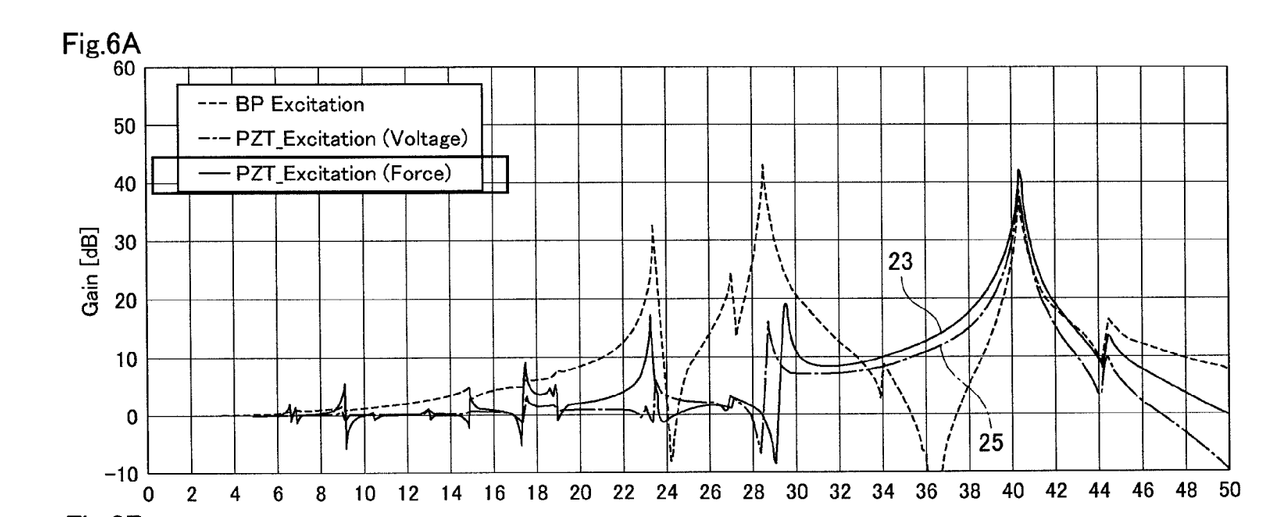
FIG. 6A is a gain diagram obtained by frequency response analysis according to the comparative example.
Figure 6B:
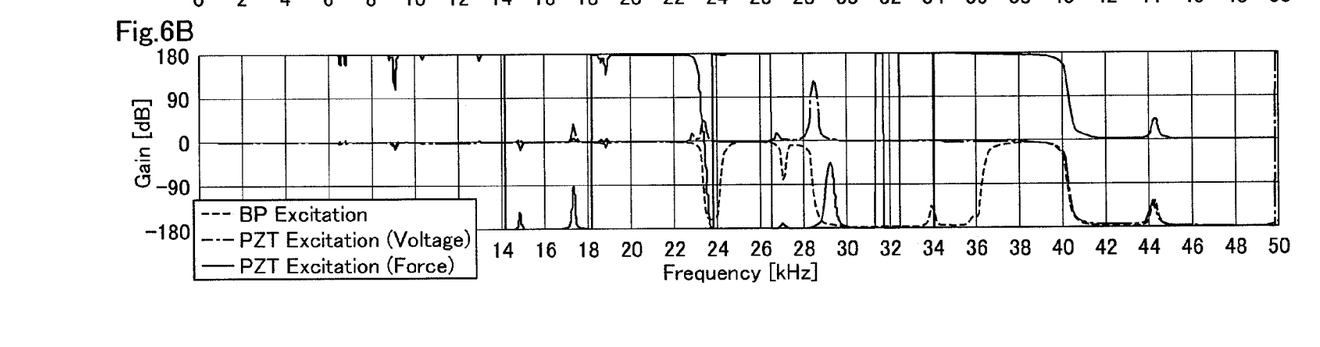
FIG. 6B is a phase diagram obtained by frequency response analysis according to the comparative example.

FIG. 2 is a perspective view illustrating the head suspension that is the object member of frequency response analysis according to the first embodiment. FIG. 3 is an enlarged perspective view illustrating the piezoelectric element on the tongue and the surrounding area of the head suspension of FIG. 2. FIG. 4 is an enlarged perspective view illustrating the same area as FIG. 3 of a head suspension according to the comparative example. FIGS. 5A and 5B are a gain diagram and a phase diagram obtained by frequency response analysis according to the first embodiment. FIGS. 6A and 6B are a gain diagram and a phase diagram obtained by frequency response analysis according to the comparative example.

As illustrated in FIG. 2, the head suspension 1 comprises a base plate 3, a load beam 5 and a flexure 9 supporting a head 7. The load beam 5 includes a rigid portion 11 and a resilient portion 13.

The flexure 9 includes read/write wirings and a tongue on which the head 7 is attached to be connected to the read/write wirings. The flexure 9 is fixed to or supported by the load beam 5. The piezoelectric element is fixed or arranged on the tongue of the flexure 9.

As illustrated in FIG. 3, a pair of piezoelectric elements 17A and 17B are fixed on the tongue 15 of the flexure 9. When voltage is applied to the piezoelectric elements 17A and 17B, the head 7 supported by the tongue 15 is slightly moved in a sway direction or a widthwise direction of the head suspension 1.

In the reaction force applying step S3, above-mentioned reaction force is applied to the piezoelectric elements 17A and 17B, as described by minute numerous arrows in FIG. 3.

In the comparative example illustrated in FIG. 4, exciting force of 1 gf is applied to each edge of the piezoelectric elements 17A and 17B.

FIG. 5 shows the result of the frequency response analysis using mode superposition method according to the reaction force application of FIG. 3. FIG. 6 shows the result of the frequency response analysis using mode superposition method according to the exciting force application of FIG. 4.

In the frequency response analysis of the first embodiment according to the condition as illustrated in FIG. 3, the vibration property exhibits as illustrated in FIG. 5. As is apparent from FIG. 5, the vibration property 19 based on the reaction force application virtually overlaps with the vibration property 21 naturally exhibited by applying voltage to the piezoelectric elements. Namely, the first embodiment accurately obtains the vibration property.

On the other hand, in the frequency response analysis of the comparative example according to the condition as illustrated in FIG. 4, the vibration property exhibits as illustrated in FIG. 6. As is apparent from FIG. 6, the vibration property 23 based on the exciting force application deviates from the vibration property 25 exhibited by applying voltage to the piezoelectric elements. The comparative example cannot accurately obtain the vibration property.

Both FIGS. 5 and 6 show the result of the frequency response analysis using mode superposition method and therefore the calculation can be performed in a short time, within 10 minutes. But as is apparent from the comparison between FIGS. 5 and 6, the first embodiment accurately obtains the vibration property, whereas the comparative example reduces the accuracy of obtaining the vibration property.

Figure 7:
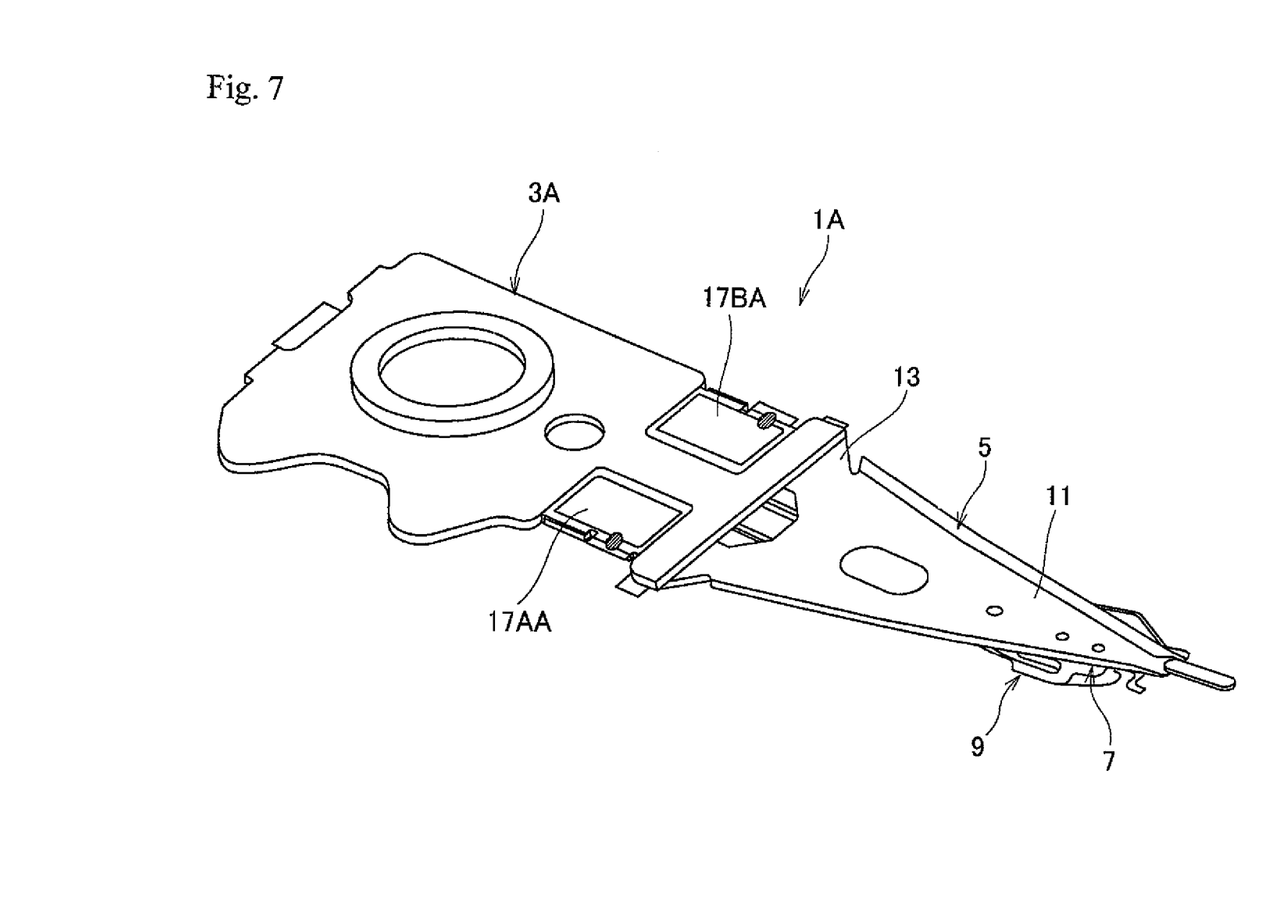
FIG. 7 is a perspective view illustrating a head suspension according to the modified embodiment.

FIG. 7 is a perspective view illustrating a head suspension according to a modified embodiment.

In the head suspension 1A of the modified embodiment, piezoelectric elements 17AA and 17BA are fixed or arranged between a base plate 3A and a load beam 5A. The other components are the same as the head suspension illustrated in FIG. 2, and the corresponding components between FIG. 2 and FIG. 7 are given the same numerals.

Figure 8A:
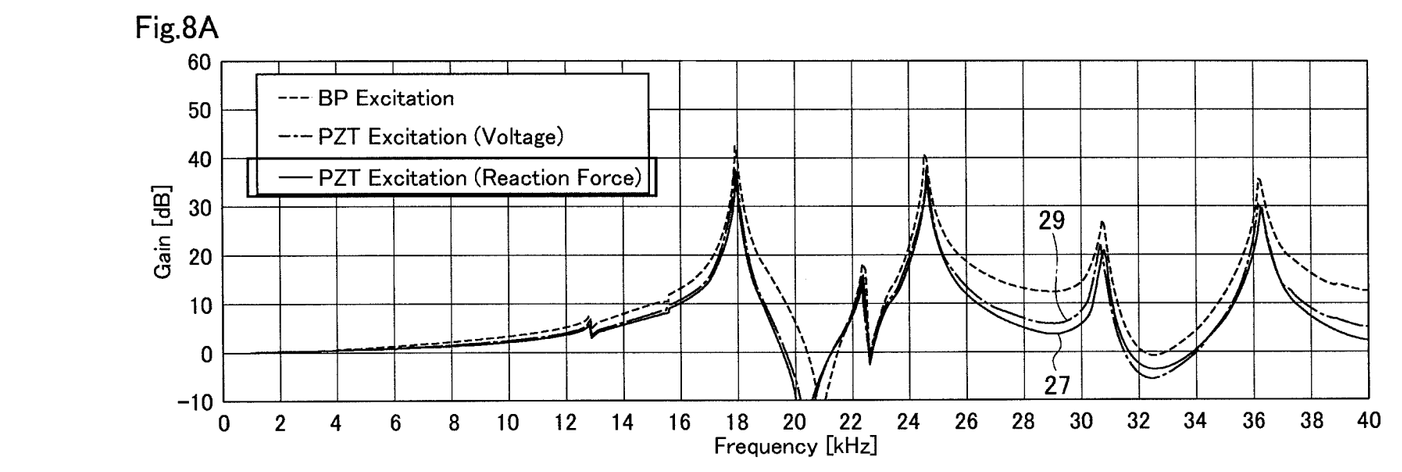
FIG. 8A is a gain diagram obtained by frequency response analysis according to the modified embodiment.
Figure 8B:
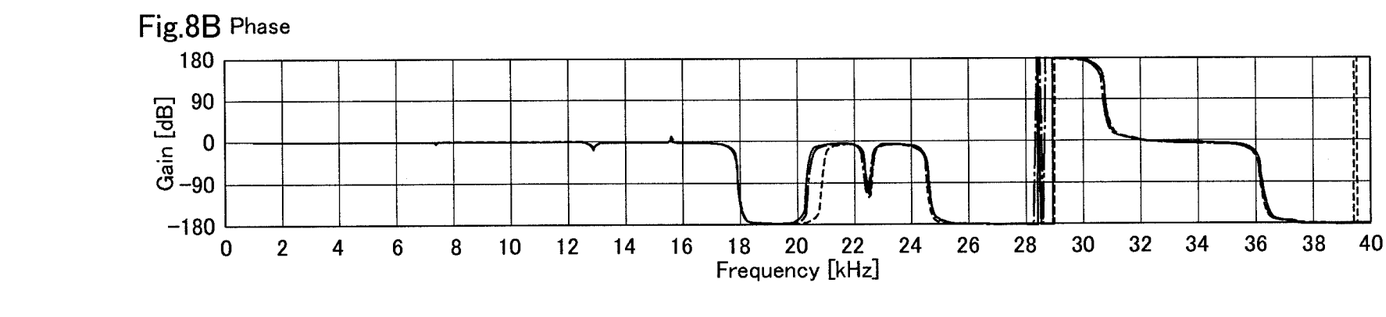
FIG. 8B is a phase diagram obtained by frequency response analysis according to the modified embodiment.

FIG. 8 shows the vibration property of the head suspension 1A, obtained by using the frequency response analysis illustrated in FIG. 1. FIG. 8A is a gain diagram and 8B is a phase diagram.

As is apparent from FIG. 8, the vibration property 27 of reaction force application virtually overlaps with the vibration property 29 naturally exhibited by applying voltage to the piezoelectric elements. Namely, the modified embodiment accurately obtains the vibration property.

Figure 9A:
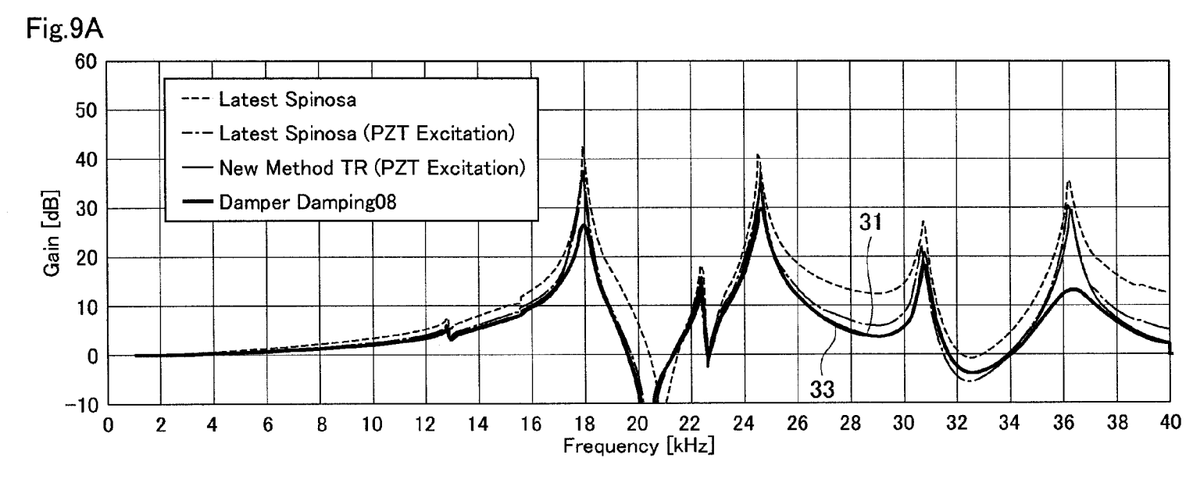
FIG. 9A is a gain diagram obtained by frequency response analysis according to the comparative example.
Figure 9B:
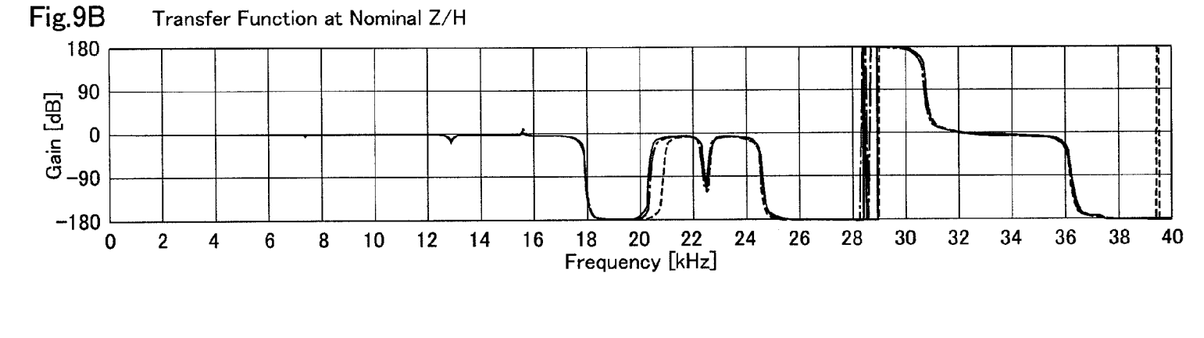
FIG. 9B is a phase diagram obtained by frequency response analysis according to the comparative example.

FIG. 9 shows the vibration property of the head suspension having a damper material at the rigid portion of the load beam, obtained by using the frequency response analysis illustrated in FIG. 1.

As is apparent from FIG. 9, the vibration property 31 of reaction force application virtually overlaps with the vibration property 33 naturally exhibited by applying voltage to the piezoelectric elements. Namely, the another modified embodiment accurately obtains the vibration property.

As mentioned above, the present invention accurately obtains vibration property within short time by using the frequency response analysis illustrated in FIG. 1, regardless of the position of the piezoelectric elements or existence of the damper material.

Each method for analyzing vibration property of a member according to the above-identified embodiments is used for analyzing the head suspension 1 or 1A. The head suspension 1 (1A) includes a head 7 and piezoelectric elements 17A (17AA) and 17B (17BA) for moving the head 7 according to voltage application. The method for analyzing vibration property comprises a displacement obtaining step S1 obtaining displacement of each node points of the piezoelectric elements 17A (17AA) and 17B (17BA) by voltage application to the piezoelectric elements 17A (17AA) and 17B (17BA), a reaction force obtaining step S2 eliminating the voltage application and obtaining reaction force of each node points of the piezoelectric elements 17A (17AA) and 17B (17BA) by applying obtained displacement to each node points, a reaction force applying step S3 eliminating the displacement and applying the obtained reaction force to each node point of the piezoelectric elements 17A (17AA) and 17B (17BA), and an analyzing step S4 performing frequency response analysis by using mode superposition method according to applied reaction force.

According to the method for analyzing vibration property, as illustrated in FIG. 5, 8 or 9, the vibration property 19, 27 or 31 based on the reaction force application virtually overlaps with or approximates to the natural vibration property 21, 29 or 33 exhibited by applying voltage to the piezoelectric elements. Namely, the method accurately obtains the vibration property.

Each head suspension 1 (1A) of the abovementioned embodiments comprises has the load beam 5 (5A), flexure 9 and piezoelectric elements 17A (17AA) and 17B (17BA). The load beam 5 (5A) includes the rigid portion 11 and the resilient portion 13 through which the base end of the rigid portion 11 is supported with the base plate 3 (3A). The flexure 9 is supported by the load beam 5 (5A) and has the tongue 15 on which the head 7 is attached to be connected to the read/write wirings. In the head suspension 1A, the piezoelectric elements 17AA, 17BA are arranged or fixed between the base plate 3A and the load beam 5A. In the head suspension 1, the piezoelectric elements 17A and 17B are arranged or fixed on the tongue 15. These piezoelectric elements 17A and 17B or 17AA and 17BA enable the head 7 to move slightly in the sway direction relative to the base plates 3 and 3A. According to the reaction force based on the voltage application to these piezoelectric elements 17A, 17B, 17AA and 17BA, the frequency response analysis of the head suspensions 1 and 1A is performed.

According to the head suspensions 1 and 1A of each embodiments, accurate vibration property can be obtained as illustrated in FIGS. 5, 8 and 9, in which the vibration property 19, 27 and 31 based on reaction force application virtually overlaps with the natural vibration property 21, 29 and 33 exhibited by applying voltage to the piezoelectric elements.

The method for analyzing vibration property illustrated in FIG. 1 can be used for other member than head suspension only if the member has a moving portion moved by voltage-applied piezoelectric elements.

Other than above-mentioned embodiment, it is also preferable that reaction force of each node points of the piezoelectric element is obtained by voltage application to the piezoelectric element in the first obtaining step, displacement of each node point of the piezoelectric element is obtained according to the obtained reaction force in the second obtaining step, obtained displacement is applied to each node point of the piezoelectric element in the applying step, and the vibration propagation analysis is performed by using mode superposition method in the analyzing step.

Besides it, it is also preferable that reaction force or displacement of each node points of the piezoelectric element is obtained by voltage application to the piezoelectric element in the obtaining step, the reaction force or the displacement is applied to each node points in the applying step, and the vibration propagation analysis is performed by using mode superposition method in the analyzing step.

The present invention is also applicable to a head suspension having a single piezoelectric element.

What is claimed is:

1. A method for analyzing vibration property of a member including a moving portion and a piezoelectric element that moves the moving portion according to voltage application, the method comprising:
   an obtaining step obtaining reaction force or displacement of each node point of the piezoelectric element by voltage application to the piezoelectric element;
   an applying step eliminating the voltage application and applying the obtained reaction force or the displacement to each node point of the piezoelectric element; and
   an analyzing step performing frequency response analysis by using mode superposition method according to the applied reaction force or the displacement.

2. A method for analyzing vibration property of a member having a moving portion and a piezoelectric element that moves the moving portion according to voltage application, the method comprising:
   a first obtaining step obtaining one of reaction force and displacement of each node point of the piezoelectric element by voltage application to the piezoelectric element;
   a second obtaining step eliminating the voltage application and obtaining the other of the displacement and the reaction force of each node point of the piezoelectric element by applying the obtained one of the reaction force and the displacement;
   an applying step eliminating the applied one of the reaction force and displacement and applying the obtained other of the displacement and the reaction force to each node point; and
   an analyzing step performing frequency response analysis by using mode superposition method according to the applied other of the reaction force and the displacement applied to each node point.

3. The method for analyzing vibration property of the member of claim 1, wherein
   the member is a head suspension to be incorporated in a hard disk drive for supporting a read/write head,
   the head suspension comprises a load beam including a rigid portion and a resilient portion through which a base end of the rigid portion is supported with the base plate, a flexure is supported by the load beam and has a tongue on which the head is attached to be connected to read/write wirings,
   the piezoelectric element is arranged between the base plate and the load beam or arranged on the tongue to slightly move the head in a sway direction relative to the base plate, and
   the frequency response analysis of the head suspension is performed according to the voltage application to the piezoelectric element.

4. The method for analyzing vibration property of the member of claim 2, wherein
   the member is a head suspension to be incorporated in a hard disk drive for supporting a head,
   the head suspension comprises a load beam including a rigid portion and a resilient portion through which a base end of the rigid portion is supported with the base plate, a flexure is supported by the load beam and has a tongue on which the head is attached to be connected to read/write wirings,
   the piezoelectric element is arranged between the base plate and the load beam or arranged on the tongue to slightly move the head in a sway direction relative to the base plate, and
   the frequency response analysis of the head suspension is performed according to the voltage application to the piezoelectric element.

* * * * *